US008690811B2

(12) United States Patent
Fox

(10) Patent No.: US 8,690,811 B2
(45) Date of Patent: Apr. 8, 2014

(54) KNEE BRACE

(76) Inventor: Richard Fox, Los Angeles, CA (US)

( * ) Notice: Subject to any disclaimer, the term of this patent is extended or adjusted under 35 U.S.C. 154(b) by 404 days.

(21) Appl. No.: 13/015,284

(22) Filed: Jan. 27, 2011

(65) Prior Publication Data

US 2012/0197170 A1     Aug. 2, 2012

(51) Int. Cl.
*A61F 5/00*     (2006.01)

(52) U.S. Cl.
USPC ................................ 602/26; 602/63; 128/882

(58) Field of Classification Search
USPC ................... 602/26, 62–63, 5, 20–21, 27, 60, 602/64–65; 2/24; 128/882
See application file for complete search history.

(56) References Cited

U.S. PATENT DOCUMENTS

| | | | |
|---|---|---|---|
| 1,388,772 A | | 8/1921 | Sheehan |
| 1,622,211 A | * | 3/1927 | Sheehan ............................. 2/22 |
| 3,046,981 A | * | 7/1962 | Biggs, Jr. et al. ............... 602/26 |
| 3,945,046 A | | 3/1976 | Stromgren |
| 4,366,813 A | | 1/1983 | Nelson |
| 4,425,912 A | | 1/1984 | Harper |
| 4,693,241 A | | 9/1987 | Trznadel |
| 4,805,606 A | * | 2/1989 | McDavid, III .................. 602/26 |
| 5,016,621 A | | 5/1991 | Bender |
| 5,086,761 A | | 2/1992 | Ingram |
| 5,267,951 A | * | 12/1993 | Ishii ................................ 602/26 |
| 5,512,039 A | * | 4/1996 | White ............................. 602/26 |
| 5,582,584 A | | 12/1996 | Billotti |
| 7,083,596 B2 | * | 8/2006 | Saied ............................ 604/110 |
| 7,173,161 B1 | * | 2/2007 | Kandt ............................. 602/41 |
| D573,713 S | | 7/2008 | Mueller et al. |
| 2003/0204156 A1 | * | 10/2003 | Nelson et al. ................... 602/26 |

OTHER PUBLICATIONS http://www.mobilisdirect.com/c-373-thuasne-knee-sport-strap.aspx, Thuasne Knee Sport Strap, Mobilis Direct, Genuine Expertise in Healthcare & Sport, Dec. 3, 2009, 1 page.

* cited by examiner

*Primary Examiner* — Patricia Bianco
*Assistant Examiner* — Kari Petrik
(74) *Attorney, Agent, or Firm* — Christie, Parker & Hale, LLP

(57) ABSTRACT

A knee brace includes a sleeve; and a plurality of flaps including a first lateral flap coupled to a first side of the sleeve and configured to extend toward a center of the sleeve; a second lateral flap coupled to a second side of the sleeve substantially opposite to the first side and configured to extend toward a center of the sleeve and overlap with the first transverse flap; a first transverse flap and a second transverse flap coupled to a rear side of the sleeve and configured to wrap around the first side and the second side of the sleeve, respectively, and overlap the first and second lateral flaps. Additionally, the knee brace may include a lower flap as an anterior cruciate ligament support and first and second transverse straps configured to extend over the plurality of flaps.

10 Claims, 7 Drawing Sheets

KNEE BRACE

BACKGROUND

1. Field

Embodiments of the present invention generally relate to a knee brace.

2. Discussion or Related Art

Knee braces are often used by athletes and other persons engaged in physical activity to protect the knee from injury or to avoid exacerbation of an existing injury. The knee is one of the most heavily worked joints of the human body because it is used in any activity that involves movement of the leg, including, for example, running, walking, skiing, surfing, roller skating snowboarding and skateboarding. Additionally, the knee is also a common subject of injury due to the relatively high levels of stress it bears under dynamic loads that are often multiples of the entire weight of the body and due to its flexibility placing it in vulnerable positions. During many activities, the knee can undergo abnormal motions as a result of quick changes in direction, fatigue, uneven surfaces, or impact which can cause sprains or more serious injuries, such as dislocation or stretching or tearing of the tissues that make up the knee or fractures of the bones of and proximate the knee.

Specifically, injuries to the knee may occur from muscular imbalances, and in particular the imbalance of two of the quadriceps muscle group: the Vastus medialis oblique (VMO) muscle located on the inner aspect of the thigh and the Vastus lateralis located on the outer aspect of the thigh. Due to the Vastus lateralis being a larger muscle than the VMO and combined with the factors of the Q-angle (the angle from the hip to the midline of the patella), there is a tendency for the patella to track laterally.

Devices to protect the knee against abnormal motions have been used for many years, varying in their abilities to protect against impact, buckling, torsional damage, among others as well as their ability to provide support to the knee while still allowing for flexibility and comfort to the wearer. Simple sleeve-based knee braces are well known in the art and consist of a relatively flexible tube that a user slides onto the knee. While simple sleeve-based braces offer some protection and stability to the knee, they are often insufficient for high impact activities such as football, skiing or competitive roller skating ("roller derby"). Additionally, some knee braces include relatively rigid metal or polymer resin strips, bands or rods extending longitudinally along the knee brace. However, such rigid members are often relatively heavy and cumbersome and do not permit normal knee flexibility. Additionally, such rigid members may not be permitted to be worn during contact sports or activities, such as football and roller derby, because the rigid member may injure another competitor.

SUMMARY

Accordingly to aspects of the present invention, a knee brace is provided that allows a user to easily support her knee without the need for extra tape or burdensome rigid metal/composite bars. Further, aspects of the present invention allow the user to strap the knee brace is such a way as to imitate a taping technique of an experienced doctor of chiropractic, athletic trainer or other specialist.

In one embodiment, a knee brace is provided including a sleeve and a plurality of flaps including a first lateral flap coupled to a first side of the sleeve and configured to extend toward a center of the sleeve; a second lateral flap coupled to a second side of the sleeve substantially opposite to the first side and configured to extend toward a center of the sleeve and overlap with the first transverse flap; a first transverse flap and a second transverse flap coupled to a rear side of the sleeve and configured to wrap around the first side and the second side of the sleeve, respectively, and overlap the first and second lateral flaps.

In one embodiment, the knee brace further includes a lower flap coupled to a bottom portion of the sleeve; and first and second transverse straps coupled to the lower flap and configured to extend over the first and second lateral flaps and over the first and second transverse flaps. Additionally, the knee brace may include an upper strap coupled to an upper portion of the sleeve and configured to wrap around the sleeve.

In one embodiment, a plurality of fasteners are on the knee brace, wherein one of the fasteners corresponds to each of the plurality of flaps. The fasteners may include a hook and loop fastener and each of the flaps may be a stretchable material. In embodiments, an exterior-facing surface of the first lateral flap has a fastener configured to mate with a fastener on an interior-facing surface of the second lateral flap and/or a fastener on an interior-facing surface of the first or second transverse flap.

In one embodiment, the first lateral flap has a first edge that extends at an angle from the first side of the sleeve toward a center of the sleeve and a second edge that extends in a direction from a knee toward a thigh of a user when the knee brace worn. Further, the second lateral flap may be generally triangular. Additionally, in one embodiment, an edge of the first lateral flap and an edge of the second lateral flap together generally form a V-shape when the first and second lateral flaps are coupled to the sleeve.

DETAILED DESCRIPTION

Embodiments of the present invention are generally directed to a knee brace having a flap and strap configuration for supporting a wearer's knee without encumbering the wearer or without significantly restricting her range of movement. As described in more detail below, the knee brace configuration resembles a support structure that can be provided by athletic tape, but further provides impact protection for the knee and does not require a skilled and trained athletic trainer to be applied.

Figure 1:
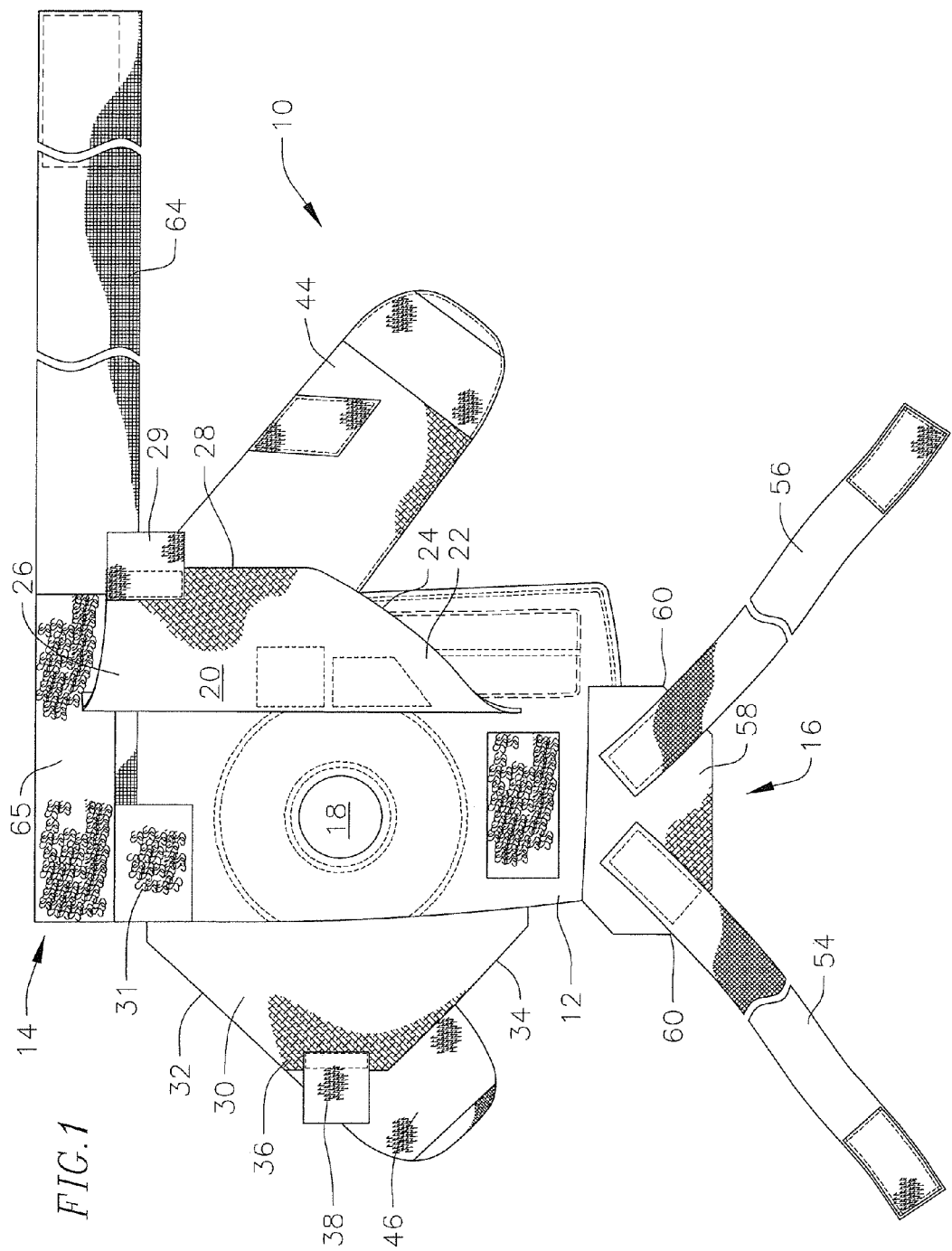
FIG. 1 is a front view of a knee brace in a ready configuration according to an exemplary embodiment of the present invention.
Figure 2:
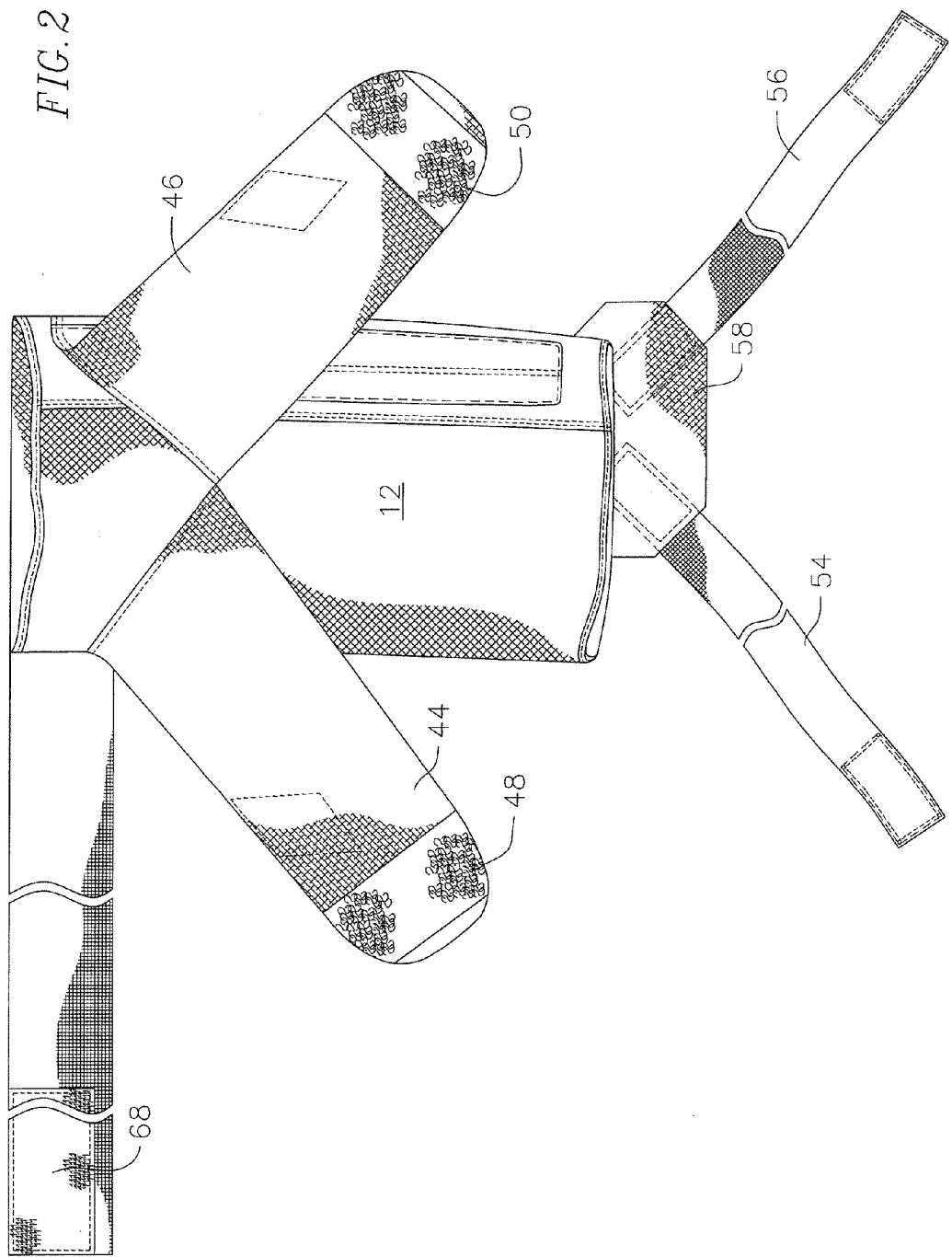
FIG. 2 is a rear view of the knee brace of FIG. 1.

With reference now to FIGS. 1 and 2, an embodiment of a knee brace 10 includes a sleeve 12 that serves generally as a base for the knee brace. The sleeve 12 has an open top end 14 and an open bottom end 16 that allows it to slide over a wearer's leg up to around her knee area. The sleeve 12 may be made from a relatively flexible material that is also stretchable, thereby allowing it to fit tightly around the wearer's lower thigh, knee, and upper shin and provide support thereto. For example, the sleeve 12 may be neoprene, but the sleeve is not limited thereto. In one embodiment, the sleeve 12 may have an opening 18 that is configured to be generally aligned with the wearer's patella to allow for increased flexibility of the sleeve, to provide increased comfort for the wearer, and to avoid compression of the patella on the femoral condyles to avoid patellofemoral pain syndrome (PFPS).

In one embodiment, the sleeve 12 is a single integral piece made from a single material, but it will be appreciated that the sleeve is not limited thereto and could be multiple pieces coupled together and be made from two or more materials. For example, the sleeve 12 may have a mesh rear portion that is configured to be located generally adjacent to the back of the wearer's knee, the rear portion being thinner than the rest of the sleeve to allow for increased flexibility. Additionally, the sleeve may include flexible inserts to provide stability and resistance to impact.

Embodiments of the knee brace include a variety of flaps coupled to the sleeve 12 configured to simulate taping a knee with athletic tape and a plurality of straps to provide additional support for the wearer and to help maintain the brace in a proper position and location on the wearer. The location and orientation of the flaps and straps of the knee brace 10 will be described in detail below generally with respect to the sleeve 12. As defined herein, "lateral" means generally a side of the sleeve 12 when the knee brace 10 is worn. Additionally, "top" or "upper" generally refers to a portion of the knee brace 10 closer to or on a wearer's thigh and "bottom" or "lower" generally refers to a portion of the knee brace closer to or on a wearer's shin when the knee brace 10 is worn. Similarly, "front," "rear," "interior-facing," and "exterior-facing" refer to portions of the knee brace or general orientations with respect to the knee brace being worn.

Figure 3:
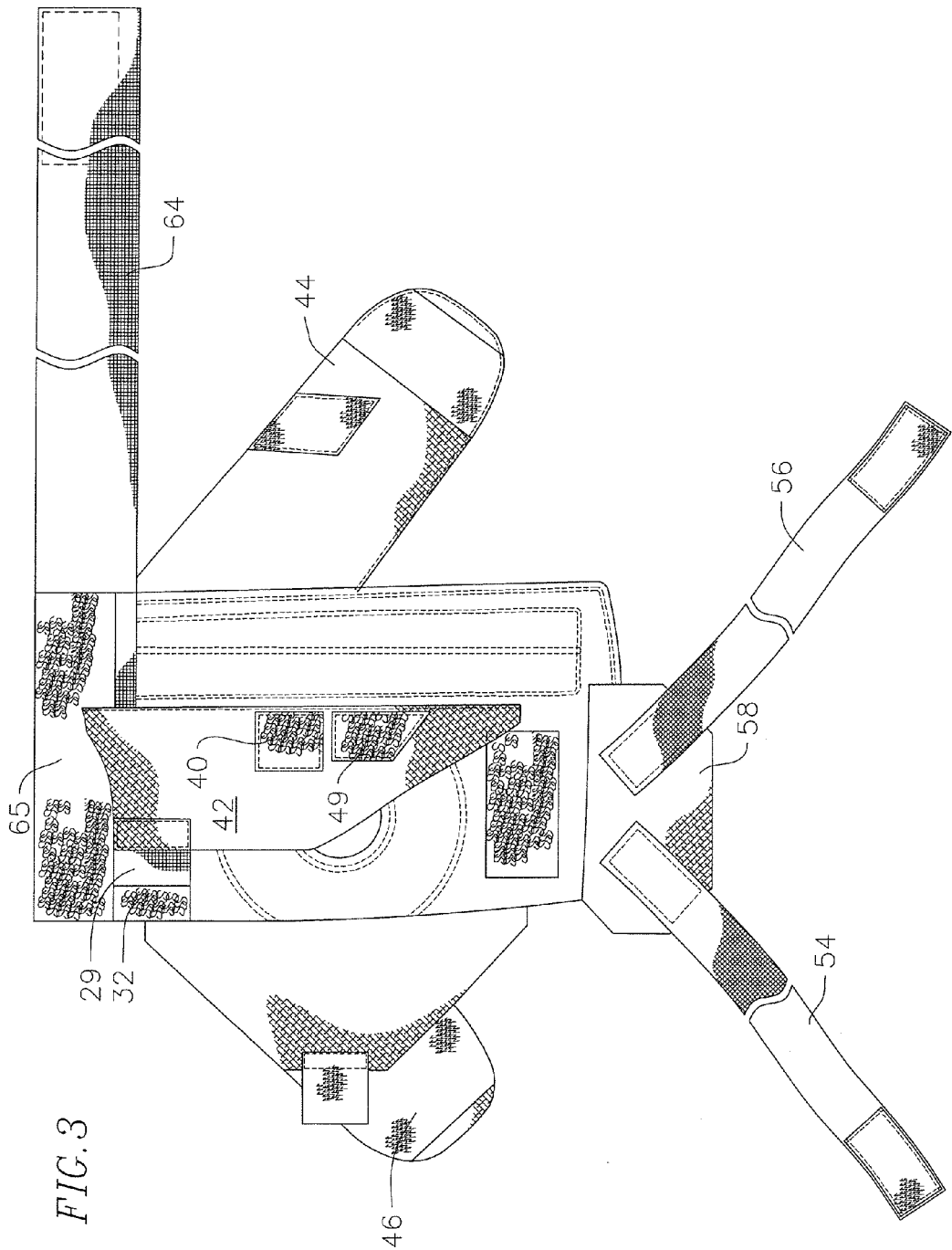
FIG. 3 is a front schematic view of the knee brace of FIG. 1 with a first lateral flap in a use position.

With reference to FIGS. 1 and 3, the knee brace 10 includes a first lateral flap 20 coupled along a lateral portion of the sleeve 12. The first lateral flap 20 is shaped such that when the knee brace 10 is worn a lower portion 22 having an angled edge 24 extends from the side of the sleeve 12 upward in a direction generally towards the open top end 14 and an upper portion 26 integral with the lower portion and having an edge 28 extending substantially vertically towards an upper portion of the brace 10.

As shown in FIG. 3, the first lateral flap is configured to extend across the front of the sleeve to generally cover about a front half of the wearer's knee region. An upper region of the edge 28 includes a fastener 29 that is adapted to be coupled to a fastener 31 on the sleeve to fix the first lateral flap 20 in a proper orientation on the knee brace 10. In one embodiment, all of the fasteners of the knee brace 10 may be hook and loop fasteners, such as VELCRO®, but it will be appreciated that the fasteners could be snap buttons, adhesive fasteners or any other suitable fastener. In general, the first lateral flap 20 is designed to support the VMO muscle by offering resistance to the VMO muscle during movement of the knee because the VMO is particularly important for stabilizing the patella during walking, running, kicking, roller skating, and other similar activities.

Figure 4:
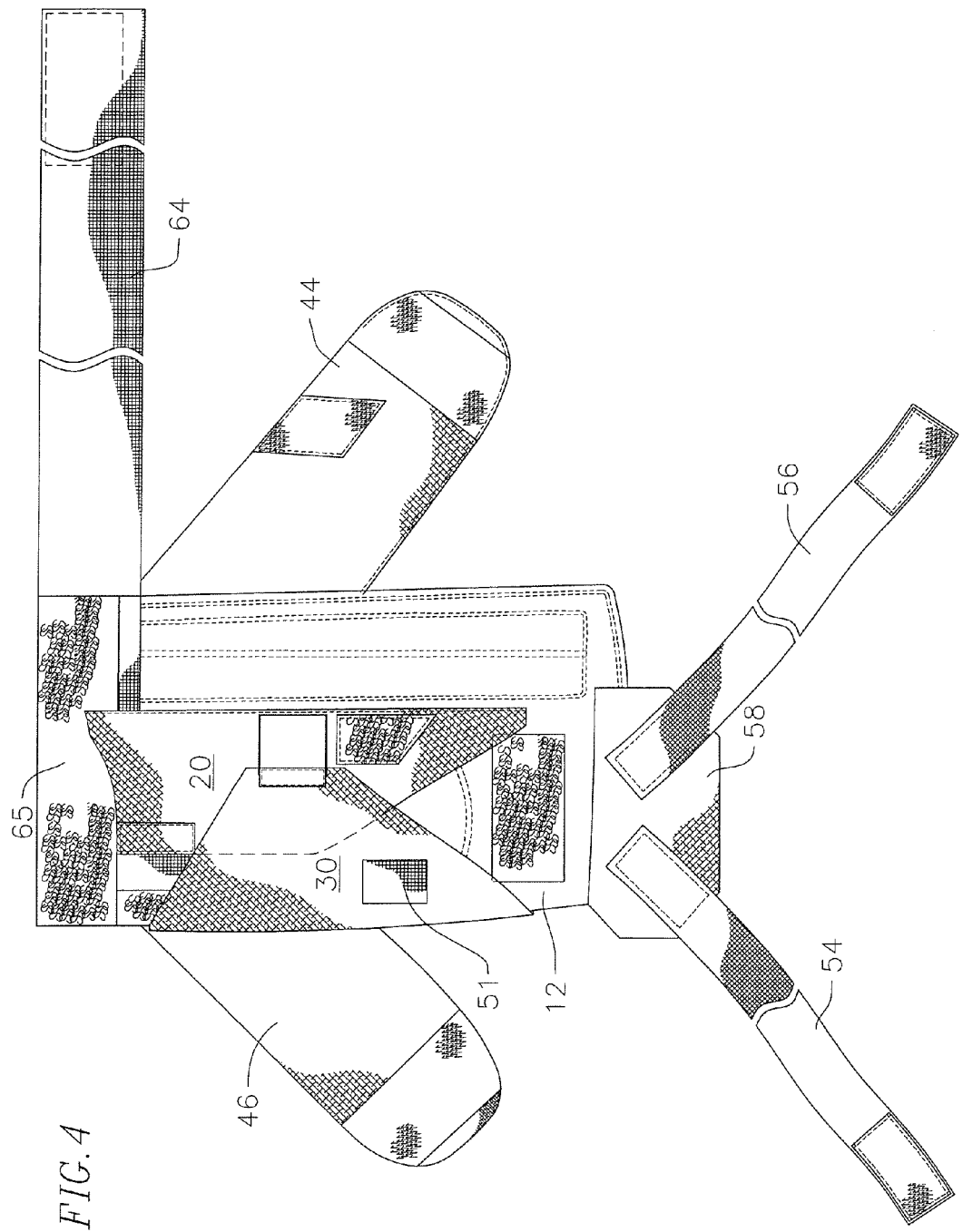
FIG. 4 is a front schematic view of the knee brace of FIG. 1 with a first and second lateral flaps in a use position.

With reference now to FIGS. 1 and 4, a second lateral flap 30 is located on a lateral portion of the sleeve 12 generally opposite to the first lateral flap 20. The second lateral flap 30 is substantially triangular or frustoconical having angled edges 32, 34 extending from a side of the sleeve 12 toward the opening 18 with a flat edge 36 between the two angled edges. As shown in FIG. 4, the second lateral flap 30 is configured to extend over the first lateral flap 20 and has a fastener 38 adapted to be coupled to a fastener 40 on an exterior facing surface 42 of the first lateral flap. In general, the second lateral flap 30 simulates the McConnell knee taping technique and provides resistance against lateral tracking of the patella to keep the patella in place. As shown in FIG. 4, when the first and second lateral flaps 20, 30 are fastened in a use position, the lower edges generally form a "V" shape.

Figure 5:
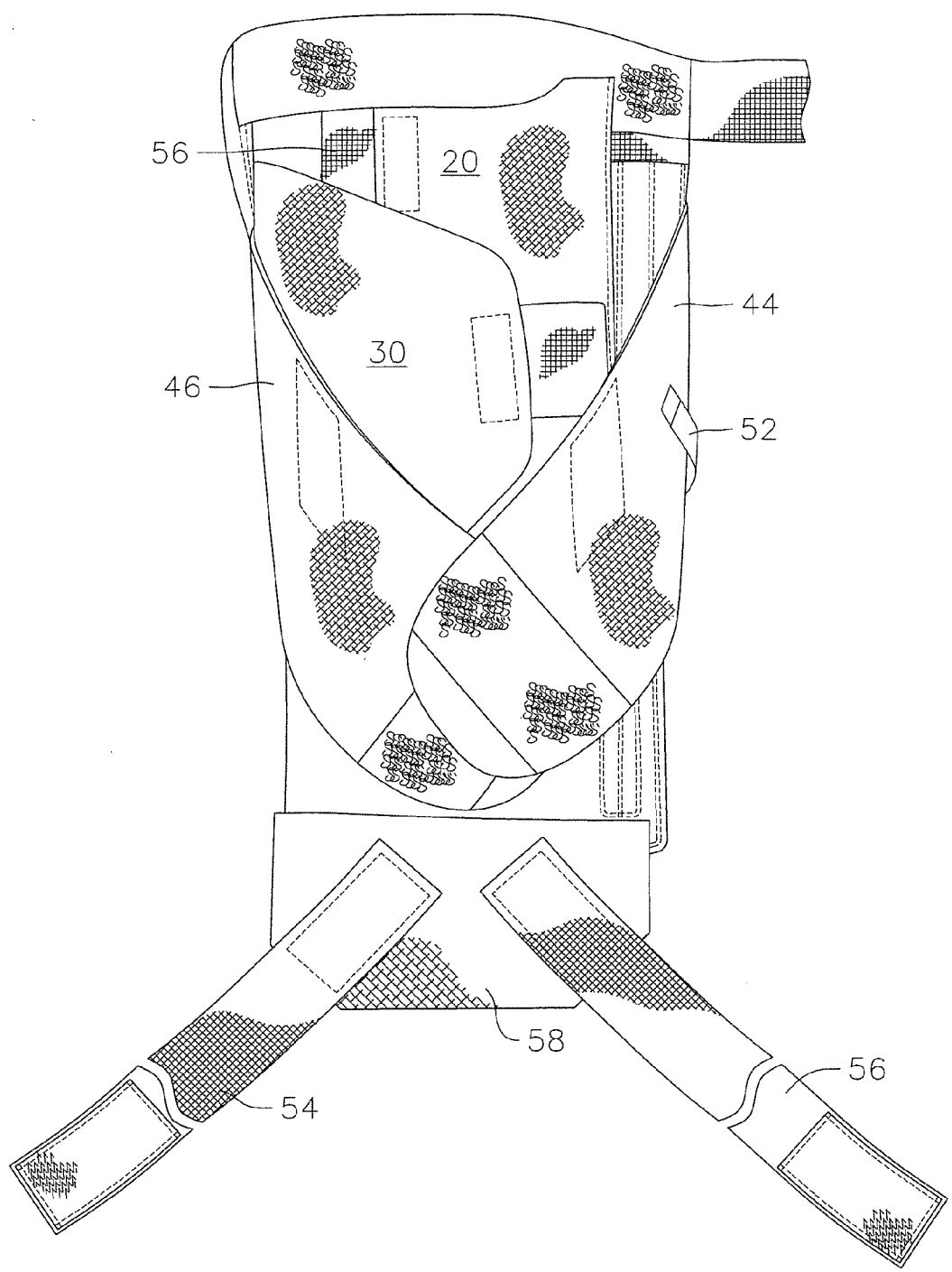
FIG. 5 is a front schematic view of the knee brace of FIG. 1 with first and second transverse flaps extending over the first and second lateral flaps in a use position.

With reference now also to FIG. 2, the knee brace 10 includes a pair of transverse flaps 44, 46 attached to the rear side of the sleeve 12. As shown in the figure, the transverse flaps 44, 46 are attached to the sleeve 12 so that they extend generally from a center of the sleeve toward a side of the sleeve downwardly at about a 45 degree angle from the vertical. The transverse flaps 44, 46 have a length configured to allow the straps to be wrapped around the sides of the sleeve 12 and attached to the front of the sleeve over the first and second lateral flaps 20, 30 as shown in FIG. 5.

In general, the transverse flaps 44, 46 are configured to provide additional compression and support to the medial and lateral collateral ligaments and the medial and lateral menisci.

In one embodiment, an interior-facing surface of the transverse flaps 44, 46 has a fastener 48, 50 respectively coupleable to a fastener 49, 51 on the exterior-facing surface of the first and second flaps 20, 30. With continued reference to FIG. 5, one of the transverse flaps 46 can overlap the other transverse flap 44 when each flap is secured over the lateral flaps 20, 30. Each of the transverse flaps 44, 46 may also include a loop 52 configured to accommodate a transverse strap 54, 56, as described in more detail below.

Figure 6:
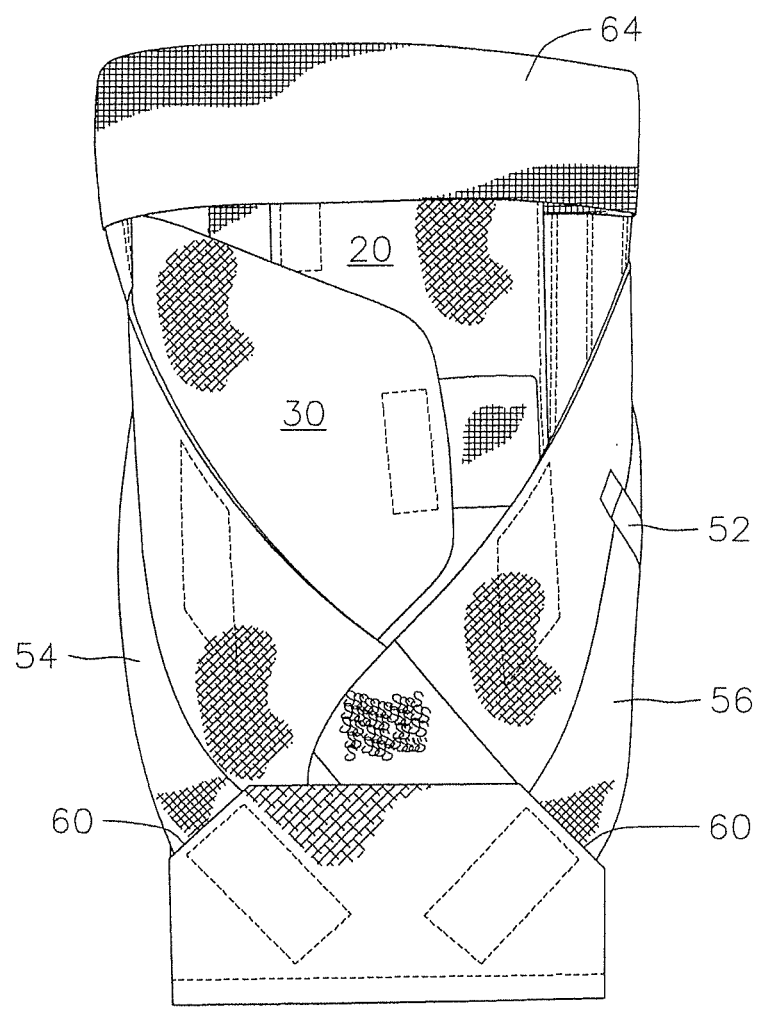
FIG. 6 is a front schematic view of the knee brace of FIG. 1 fully configured in a use position.

Referring again to FIG. 1, a lower flap 58 is coupled to the bottom region of the sleeve 12 and is configured to pivot about an axis substantially parallel to the bottom edge of the sleeve. With reference to FIG. 6, the lower flap can be pivoted to cover the distal ends of the first and second transverse flaps 44, 46. The lower flap 58 has angled upper edges 60 which accommodate first and second transverse straps 54, 56, as described in more detail below. In general, the lower flap 58 provides support for the anterior cruciate ligament, particularly with respect to translation of the femur and tibia movements.

The first and second transverse straps 54, 56 are attached to an interior-facing surface of the lower flap 58. In one embodiment, the straps 54, 56 may be attached at an angle in a direction away from the center of the sleeve 12 toward a respective side of the sleeve, i.e., each strap extends away from the other one. The first and second straps 54, 56 can extend through a loop 52 on the first and second transverse flaps 44, 46, around the rear of sleeve 12 such that they intersect, and then around to the front of the sleeve where they can be attached by fasteners 62 on the transverse flaps or on an upper fastener 66. The loops 52 are optional, but serve to generally maintain the transverse straps 54, 56 in their desired orientation after they have been fastened into place. In the general, the first and second transverse straps 54, 56 imitate the hamstrings and provide additional support to the anterior cruciate ligament with respect to translation of the femur and tibia. The straps may eliminate the need for heavier and more burdensome hinge and metal/composite reinforcements of hard braces.

As shown in FIG. 1, an upper strap 64 and an upper fastener 66 may be located at the upper portion of the sleeve 12. The upper strap 64 is attached to one side of the sleeve 12 and is configured to wrap around the sleeve and a user's leg to further secure the knee brace 12 and optionally some of the straps as well. In one embodiment, the upper strap 64 is made from a stretchable elastic material, but the upper strap may be made from any suitable material. The upper strap 64 may include an upper strap fastener 68 that is configured to engage the upper fastener 66.

Each of the flaps can be made from a stretchable, flexible and durable material that allows the flaps to be provide compression to the knee area to provide stability. In one embodiment, the flaps may be made from a combination of KFOAM™ and stretch KEVLAR®. However, it will be appreciated that the flaps could also be made from any other suitable material.

With reference primarily to FIGS. 3-7, an embodiment of a use configuration of the knee brace will be described. The wearer puts on the brace by sliding the sleeve 12 up her leg to her knee such that the opening 12 generally exposes her patella. As will be appreciated, the brace 10 may be used for either knee and, although it is not necessary, the configuration could be opposite depending on whether the brace is for the left knee or the right knee. Additionally, in one embodiment, each flap or pair of flaps described above could be labeled with a number to indicate an appropriate order in which the flaps should be attached to the brace.

As shown in FIG. 3, when the sleeve 12 is position on the wearer's knee, the first lateral flap 20 is folded over the sleeve 12 toward the opening 18 and is attached to the sleeve by attaching fastener 27 to fastener 31. With reference to FIG. 4, the second lateral flap 30, located generally opposite to the first lateral flap 20, can then be folded to partially cover the first lateral flap. The fastener 38 on the second lateral flap 30 can be coupled to the corresponding fastener 40 on the exterior-facing surface of the first lateral flap 20 to fix the second lateral flap in place.

With reference now to FIG. 5, each of the first and second transverse flaps 44, 46 can then be wrapped around respective sides of the knee brace 10 and over the first and second lateral flaps 20, 30. The fastener 48 on an interior-facing surface of the first transverse flap 44 can be coupled to the fastener 47 on the sleeve 12 and the fastener 50 on an interior-facing surface of the second transverse flap 46 can be coupled to the fastener 49 on the exterior facing surface of the first transverse flap.

Figure 7:
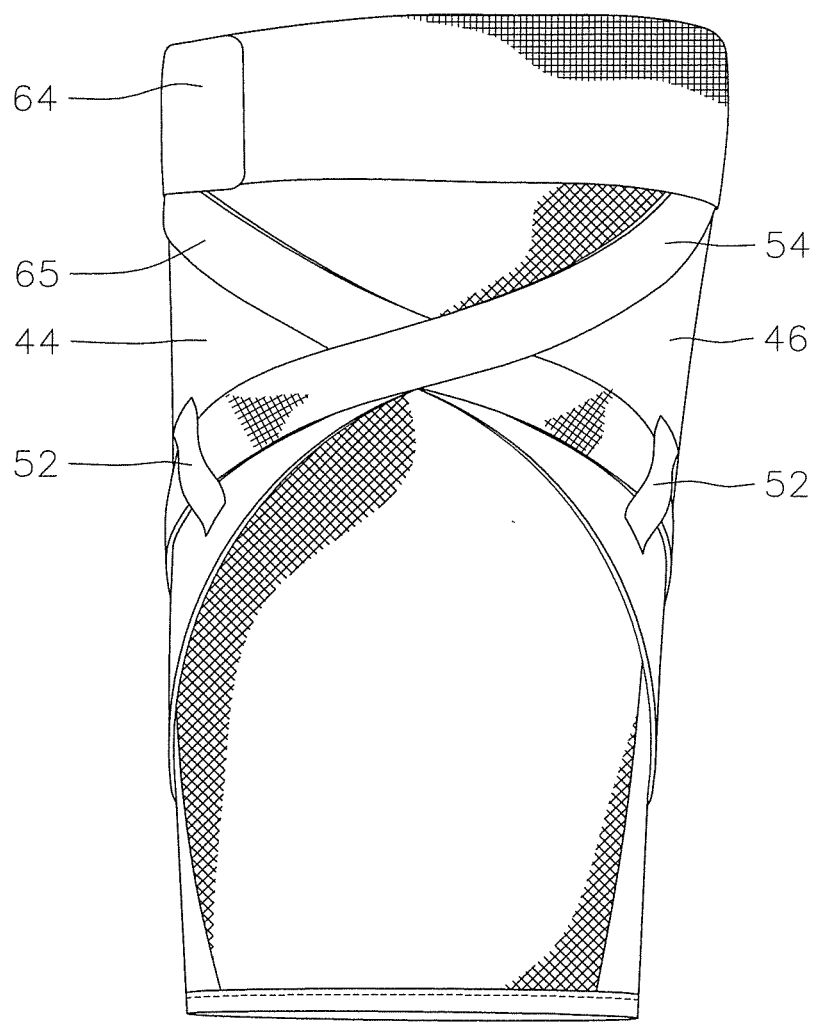
FIG. 7 is a rear schematic view of the knee brace of FIG. 1 fully configured in a use position.

Once the first and second transverse flaps 44, 46 have been fixed in place, the lower flap can be pivoted upwards to cover a bottom portion of the transverse flaps. Additionally, the first and second transverse straps 54, 56 can be inserted through respective loops 52 on the first and second transverse flaps 44, 46 and can be wrapped around the sleeve 12 from the lower flap 38 around the rear and back to the upper portion of the front of the sleeve as shown in FIGS. 6 and 7. The transverse straps 54, 56 can be attached by fasteners on an interior-facing surface to the fastener 66 on the top portion of the sleeve 12. Finally, the upper strap 64 can be wrapped around the top portion of the sleeve 12 covering a portion of the transverse straps 54, 56 and fixed to the sleeve by attaching the fastener on its interior-facing portion to the fastener 66 on the top portion of the sleeve.

Although embodiments of the invention have been shown and described, it will be appreciated by those skilled in the art that changes may be made in these embodiments without departing from the principles and spirit of the invention, the scope of which is defined in the claims and their equivalents.

What is claimed is:

1. A knee brace comprising:
a sleeve;
and a plurality of flaps comprising:
    a first lateral flap coupled to a first side of the sleeve and configured to extend toward a center of the sleeve;
    a second lateral flap coupled to a second side of the sleeve substantially opposite to the first side and configured to extend toward a center of the sleeve and overlap with the first lateral flap;
    a first transverse flap and a second transverse flap coupled to the sleeve and configured to wrap around the first side and the second side of the sleeve, respectively, wherein both the first transverse flap and the second transverse flap are configured to overlap both the first and second lateral flaps; and
    a lower flap coupled to a bottom portion of the sleeve; and
first and second transverse straps coupled to the lower flap and configured to extend over the first and second lateral flaps and over the first and second transverse flaps.

2. The knee brace of claim 1, further comprising an upper strap coupled to an upper portion of the sleeve and configured to wrap around the sleeve.

3. The knee brace of claim 1, further comprising a plurality of fasteners, wherein one of the fasteners corresponds to each of the plurality of flaps.

4. The knee brace of claim 3, wherein the fasteners comprise a hook and loop fastener.

5. The knee brace of claim 1, wherein each of the flaps comprises a stretchable material.

6. The knee brace of claim 1, wherein the first lateral flap has a first edge that extends at an angle from the first side of the sleeve toward a center of the sleeve and a second edge that extends in a direction from a knee toward a thigh of a user when the knee brace worn.

7. The knee brace of claim 1, wherein the second lateral flap is generally triangular.

8. The knee brace of claim 1, wherein an edge of the first lateral flap and an edge of the second lateral flap together generally form a V-shape when the first and second lateral flaps are fastened to the sleeve.

9. The knee brace of claim 1, wherein an exterior-facing surface of the first lateral flap has a fastener configured to mate with a fastener on an interior-facing surface of the second lateral flap.

10. The knee brace of claim 1, wherein an exterior-facing surface of the first lateral flap has a fastener configured to mate with a fastener on an interior-facing surface of the first or second transverse flap.

* * * * *

UNITED STATES PATENT AND TRADEMARK OFFICE
CERTIFICATE OF CORRECTION

| | | |
|---|---|---|
| PATENT NO. | : 8,690,811 B2 | Page 1 of 1 |
| APPLICATION NO. | : 13/015284 | |
| DATED | : April 8, 2014 | |
| INVENTOR(S) | : Richard J. Fox | |

It is certified that error appears in the above-identified patent and that said Letters Patent is hereby corrected as shown below:

In the Claims

Column 6, line 40, Claim 6     After "brace"

Insert -- is --

Signed and Sealed this
Twentieth Day of October, 2015

Michelle K. Lee
*Director of the United States Patent and Trademark Office*